(12) United States Patent
Aylsworth et al.

(10) Patent No.: US 9,056,179 B2
(45) Date of Patent: Jun. 16, 2015

(54) HOSE CONNECTION SYSTEM FOR NARIALLY SENSITIVE DIAGNOSTIC DEVICES

(75) Inventors: Alonzo C. Aylsworth, Wildwood, MO (US); Charles R. Aylsworth, Wildwood, MO (US)

(73) Assignee: ACOBA, L.L.C., Chesterfield, MO (US)

( * ) Notice: Subject to any disclaimer, the term of this patent is extended or adjusted under 35 U.S.C. 154(b) by 2446 days.

(21) Appl. No.: 11/755,844

(22) Filed: May 31, 2007

(65) Prior Publication Data

US 2007/0277824 A1 Dec. 6, 2007

Related U.S. Application Data

(60) Provisional application No. 60/803,560, filed on May 31, 2006.

(51) Int. Cl.
| | |
|---|---|
| *A61M 16/08* | (2006.01) |
| *A61M 16/06* | (2006.01) |
| *A61M 16/00* | (2006.01) |
| *A61B 5/087* | (2006.01) |

(52) U.S. Cl.
CPC ............ *A61M 16/0666* (2013.01); *A61B 5/087* (2013.01); *A61M 16/08* (2013.01); *A61M 16/0816* (2013.01); *A61M 2016/0027* (2013.01); *A61M 2016/003* (2013.01); *A61M 2205/14* (2013.01); *A61M 2205/6027* (2013.01); *A61M 2205/6045* (2013.01); *A61M 2205/6054* (2013.01); *A61M 2205/6081* (2013.01); *A61M 2210/0625* (2013.01)

(58) Field of Classification Search
USPC ............ 128/202.27, 204.11, 204.12, 206.11, 128/207.18, 203.22, 204.28, 204.21
See application file for complete search history.

(56) References Cited

U.S. PATENT DOCUMENTS

| | | | | |
|---|---|---|---|---|
| 3,600,592 | A | * | 8/1971 | Mahan et al. ................. 250/569 |
| 4,585,399 | A | * | 4/1986 | Baier ........................ 417/477.12 |
| 5,255,672 | A | * | 10/1993 | Jinotti ....................... 128/200.26 |
| 5,323,808 | A | * | 6/1994 | Shimizu ........................ 137/594 |
| 5,746,719 | A | * | 5/1998 | Farra et al. ..................... 604/151 |
| 6,019,731 | A | * | 2/2000 | Harbrecht et al. ............. 600/532 |
| 7,455,644 | B2 | * | 11/2008 | Yamamori et al. ............ 600/532 |
| 2002/0124890 | A1 | * | 9/2002 | Murayama et al. ...... 137/565.17 |
| 2005/0005942 | A1 | * | 1/2005 | Aylsworth et al. ........ 128/207.18 |
| 2006/0042634 | A1 | * | 3/2006 | Nalagatla et al. ......... 128/207.18 |
| 2006/0150712 | A1 | * | 7/2006 | Berstis et al. .................. 73/23.2 |
| 2007/0265877 | A1 | * | 11/2007 | Rice et al. ......................... 705/2 |

* cited by examiner

*Primary Examiner* — Rachel Young
(74) *Attorney, Agent, or Firm* — Mark E. Scott; Conley Rose, P.C.

(57) ABSTRACT

Hose connection system for narially sensitive diagnostic devices. At least some of the illustrative embodiments are systems including a test device and a nasal cannula. The test device includes a first port configured to sense an attribute of airflow, and a second port configured to sense an attribute of airflow. The nasal cannula includes a first hose configured to fluidly couple on a device-end to the first port (and the first hose configured to fluidly couple between the first port and a first naris of a patient), and a second hose configured to fluidly couple on a device-end to the second port (and the second hose configured to fluidly couple between the second port and a second naris of the patient). The nasal cannula is configured such that the first hose only couples to the first port and the second hose only couples to the second port.

8 Claims, 5 Drawing Sheets

US 9,056,179 B2

HOSE CONNECTION SYSTEM FOR NARIALLY SENSITIVE DIAGNOSTIC DEVICES

CROSS-REFERENCE TO RELATED APPLICATIONS

This application claims the benefit of provisional application Ser. No. 60/803,560 filed May 31, 2006, titled "Hose connection system for narially sensitive diagnostic devices," which application is incorporated by reference herein as if reproduced in full below.

BACKGROUND

Sleep disordered breathing is common throughout the population, and some sleep disorders may be attributable to disorders of the respiratory tract. Sleep apnea may be a disorder where a person temporarily stops breathing during sleep. A hypopnea may be a period of time where a person's breathing becomes abnormally slow or shallow. In some cases, a hypopnea precedes an apnea event. Snoring may be caused by mucus build up in the upper respiratory tract, and/or excessive tissue causing cyclic full or partial blockages of the nose. Other breathing difficulties, not necessarily related to sleep but which breathing difficulties become more pronounced during sleep, may be caused by full or partial blockages of the nares, such as by a tumor or polyp.

Sleep disordered breathing and other breathing difficulties may be diagnosed in a sleep lab, or possibly by a device which the patient takes home and wears throughout the day or during sleep. For a proper diagnosis, particularly in the case of a tumor or polyp, the various ports of a test device need to be coupled to the naris for which they were intended; however, currently available nasal cannulas have device-ends (as opposed to patient-ends) that are identical and easily switched when being coupled to a test device.

BRIEF DESCRIPTION OF THE DRAWINGS

For a detailed description of the preferred embodiments of the invention, reference will now be made to tie accompanying drawings in which.

NOTATION AND NOMENCLATURE

Certain terms are used throughout the following description and claims to refer to particular system components. However, manufacturing companies may refer to various components by different names. This document does not intend to distinguish between components that differ in name but not function.

In the following discussion and in the claims, the terms "including" and "comprising" are used in an open-ended fashion, and thus should be interpreted to mean "including, but not limited to . . . ". Also, the term "couple" or "couples" is intended to mean either an indirect or direct connection. Thus, if a first device couples to a second device, that connection may be through a direct connection, or through an indirect connection via other devices and connections.

DETAILED DESCRIPTION

Figure 1:
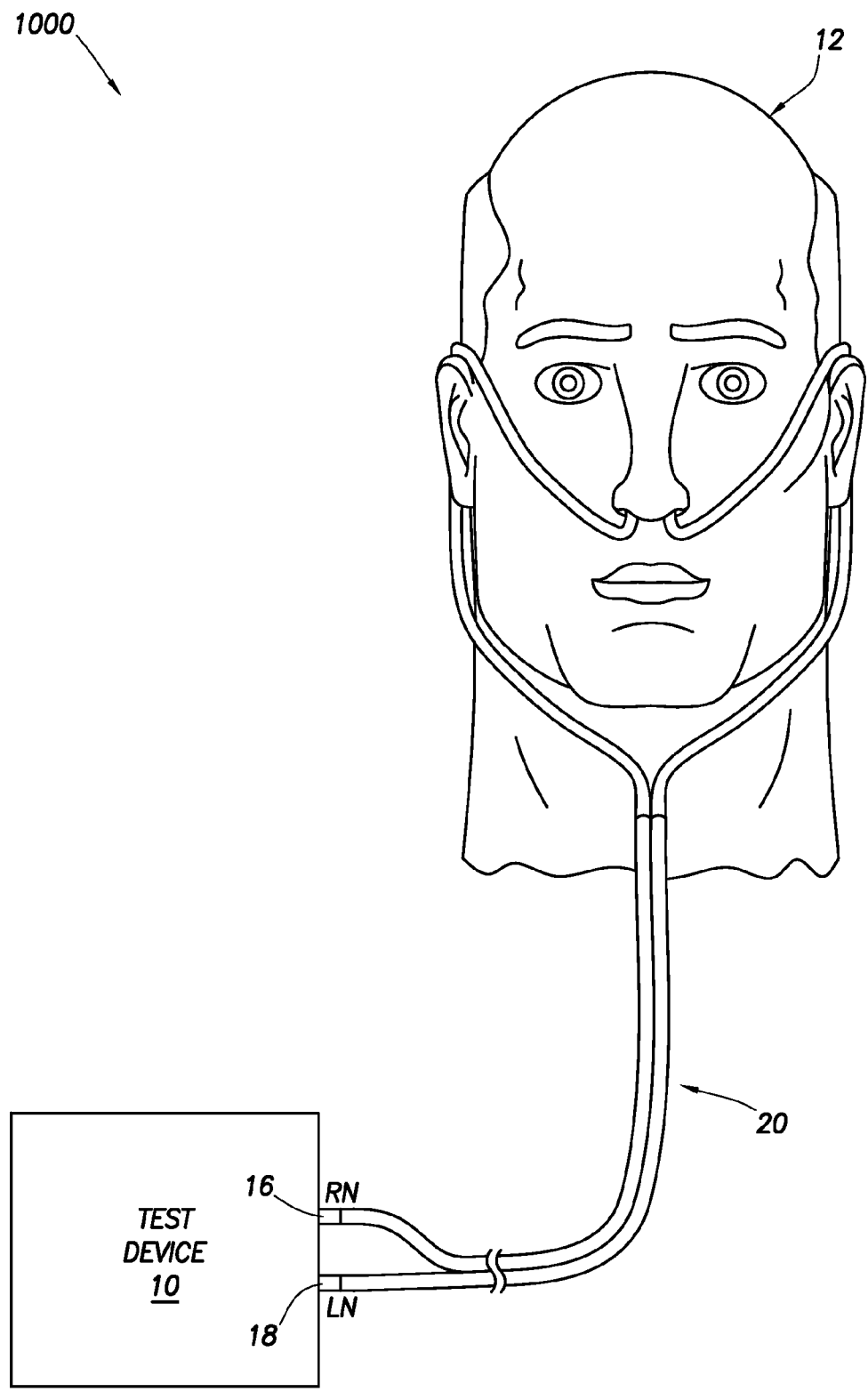
FIG. 1 illustrates a system in accordance with embodiments of the invention.

FIG. 1 illustrates a system 1000 in accordance with embodiments of the invention. In particular, FIG. 1 illustrates a test device 10. The test device 10 may be a device for sensing airflow used in a dedicated sleep lab or a hospital, or the test device 10 may be a portable possibly battery operated) device that a patient uses in their home which is used as an initial diagnostic aid in diagnosing breathing difficulties. The test device 10 may be, for example, a device such as described in issued U.S. Pat. No. 7,066,180, titled "Method and System for Measuring Airflow of Nares," which patent is incorporated by reference herein as if reproduced in full below.

The individual fluid couplings between the test device 10 and the patient 12 may be by way of a bifurcated nasal cannula 20, such a cannula having two fluidly independent pathways running between the test device 10 and the patient 12. The patient's right naris fluidly couples to a right naris port 16 and the left naris fluidly couples to a left naris port 18.

Still referring to FIG. 1, the test device 10 in accordance with at least some embodiments of the invention has the ability to log information about the absolute and/or relative inspiratory and expiratory airflow. The information regarding the inspiratory and expiratory airflow may be helpful in diagnosing certain ailments (e.g., existence of a tumor or polyp in a particular naris, head position dependent valve collapse in a particular naris). For the log to be most beneficial in diagnosis, the output port 16 for the right naris should be coupled to the right naris, and the output port 18 for the left naris should be coupled to the left nails. In accordance with at least some embodiments, the test device 10 and the bifurcated nasal cannula 20 work together to ensure that the hose for the right nails only couples to the outlet port 16 for the right naris, and the hose for the left naris only couples to the outlet port 18 for the left naris.

Figure 2:
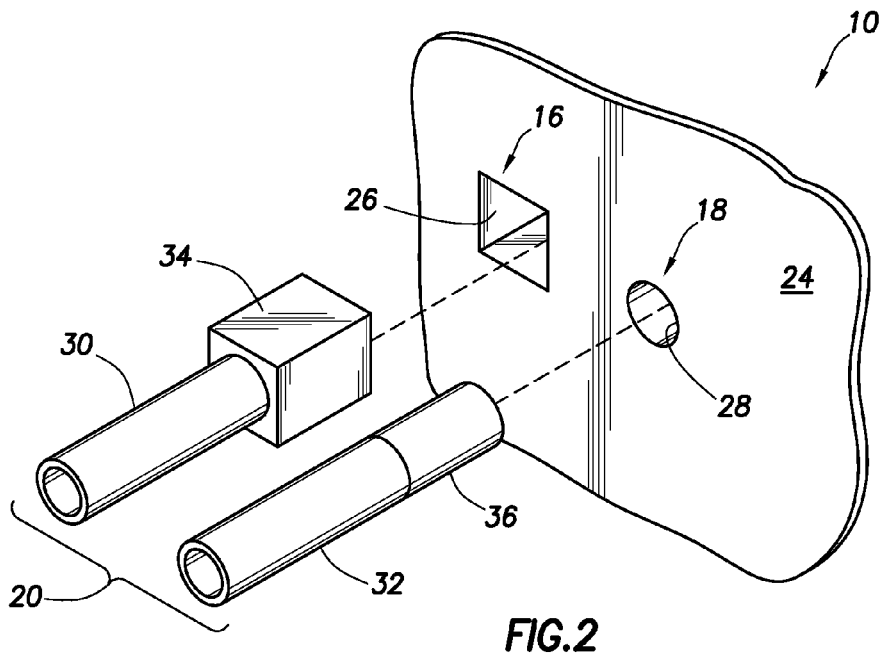
FIG. 2 illustrates hose connections in accordance with some embodiments.

Ensuring the proper coupling of the bifurcated nasal cannula 20 and the test device 10 may take many forms. In some embodiments, each hose of the bifurcated nasal cannula has a device-end (i.e., the end that couples to the test device) fitting that mates only with the appropriate outlet port. FIG. 2 illustrates a system where the device-end fittings ensure proper orientation. In particular, FIG. 2 illustrates a partial view of an exterior 24 of a test device 10. The illustrative exterior has two outlet ports 16 and 18, which in these embodiments comprise apertures 26 and 28. The apertures 26 and 28 fluidly couple to devices internal to the test device 10, such as pressure sensors and/or flow sensors. FIG. 2 also illustrates a portion of the bifurcated nasal cannula 20 comprising a first hose 30 and a second hose 32. Each of the hoses 30 and 32 have a device-end fitting 34 and 36 respectively. As illustrated in FIG. 2, the device-end fitting 34 is configured to fluidly couple to the aperture 26, but because of the difference in aperture shape the device-end fitting 34 will not couple to the aperture 28. Likewise, the device-end fitting 36 is configured to fluidly couple to the aperture 28, but because of the difference aperture shape the device-end fitting 36 will not fluidly couple the aperture 26. In this way, the bifurcated nasal cannula 20 cannot be fluidly coupled to the test device 10 in a reverse order. While FIG. 2 shows an illustrative square aperture 26 and circular aperture 28 (and corresponding device-end fittings 34 and 36), other shapes and configurations may be equivalently used. For example, the test device 10 may have one male press-fit (Luer) fitting and one female Luer fitting, with the bifurcated nasal cannula having mating Luer fittings. Any structural differences between the two hose connections that reduces the possibility of misconnecting hoses of the bifurcated nasal cannula 20 to the test device 10 may be equivalently used.

Figure 3:
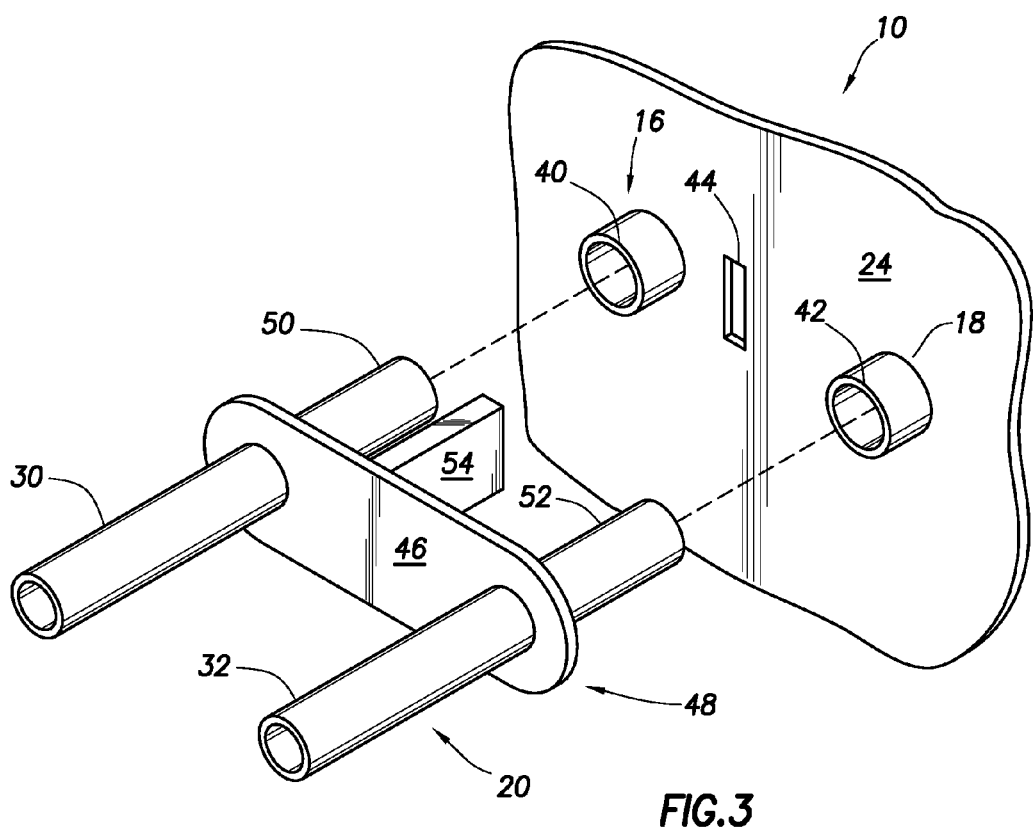
FIG. 3 illustrates hose connections in accordance with some embodiments.

FIG. 3 illustrates alternative embodiments that ensure proper coupling of the bifurcated nasal cannula 20 to the test device 10. In particular, FIG. 3 illustrates a partial view of the exterior 24 of the test device 10. The illustrative exterior has two outlet ports 16 and 18, which in these embodiments comprises male connections 40 and 42, respectively. Female connections may be equivalently used. The illustrative exterior 24 also has a key aperture 44. The connections 40 and 42 couple one each devices to internal to the test device 10, such as pressure sensors and/or flow sensors. FIG. 3 also illustrates a portion of the bifurcated nasal cannula 20 comprising a first hose 30 and second hose 32. A bracket 46 mechanically (though not fluidly) couples the hoses 30 and 32 together on the device end 48. Each of the hoses 30 and 32 has a device-end fitting 50 and 52, respectively; however, the device-end fittings 50 and 52 may be similar in these embodiments because the bracket 46 and a tab 54 work together with the aperture 44 in the test device 10 to ensure that the house is coupled in only one orientation.

As illustrated in FIG. 3, the key aperture 44 is positioned off center with respect to the outlet ports 16 and 18. Likewise, the tab 54 coupled to the bracket 46 is positioned off center with respect to the bracket 46. In this way, the device end 48 of the hose system 20 couples the hoses 30 and 32 to their respective outlet ports 16 and 18 in only one orientation—the orientation where the tab 54 extends into the key aperture 44. If a user attempts to fluidly couple the hoses 30 and 32 to the test device in a reverse orientation, the key aperture 44 will not align with the tab 54, and thus the hose system 20 will not fluidly couple to the test device 10. The long dimension of the key aperture 44, and correspondingly the long dimension of the tab 54, may be equivalently oriented at any angle. In alternative embodiments, the key aperture 44 and the tab 54 may equivalently use other corresponding shapes (e.g. circular, square, hexagonal), so long as the key aperture 44 and tab 54 allow the hose system 20 to fluidly couple to hoses 30 and 32 to the ports 16 and 18 in only one orientation. Moreover, the key aperture 44 and tab 54 need not be disposed between the outlet ports 16 and 18, and thus the key aperture 44 and the tab 54 may be equivalently above, below or outside the outlet ports 16 and 18 so long as the hose system 20 couples to the outlet ports 16 and 18 in only one orientation. Further still, the key aperture 44 and tab 54 may be centered between the ports, but the shape of the key aperture 44 and tab 54 may enable coupling in only one orientation.

When using test device 10 as a diagnostic aid, the pressures and/or airflows sensed may be relative. That is, for example, if measuring pressure as indicative of a patient's respiratory function, the pressure in each tube of the bifurcated nasal cannula is created by air being hydraulically forced into each tube during exhalation. Likewise, lower pressure associate with inhalation is created by air flowing past the patient end of the nasal cannula into the patient's nares. The amount of pressure created in each case may be dependent not only upon the respiratory effort of the patient, but also on characteristics of the hoses (e.g., inside diameter), and thus identifying the manufacturer/type of bifurcated nasal cannula may be important. Likewise in situations where airflow through the nasal cannula is sensed, exhalation by the patient causes airflow through each tube and out an atmospheric vent of the test device. Inhalation draws air through each tube. The amount of airflow, and thus the amount sensed by the test device, may be dependent not only upon respiratory effort of the patient, but also on characteristics of the hoses (e.g., internal diameter, length), and thus identifying the manufacture/type of bifurcated nasal cannula may be important.

Figure 4:
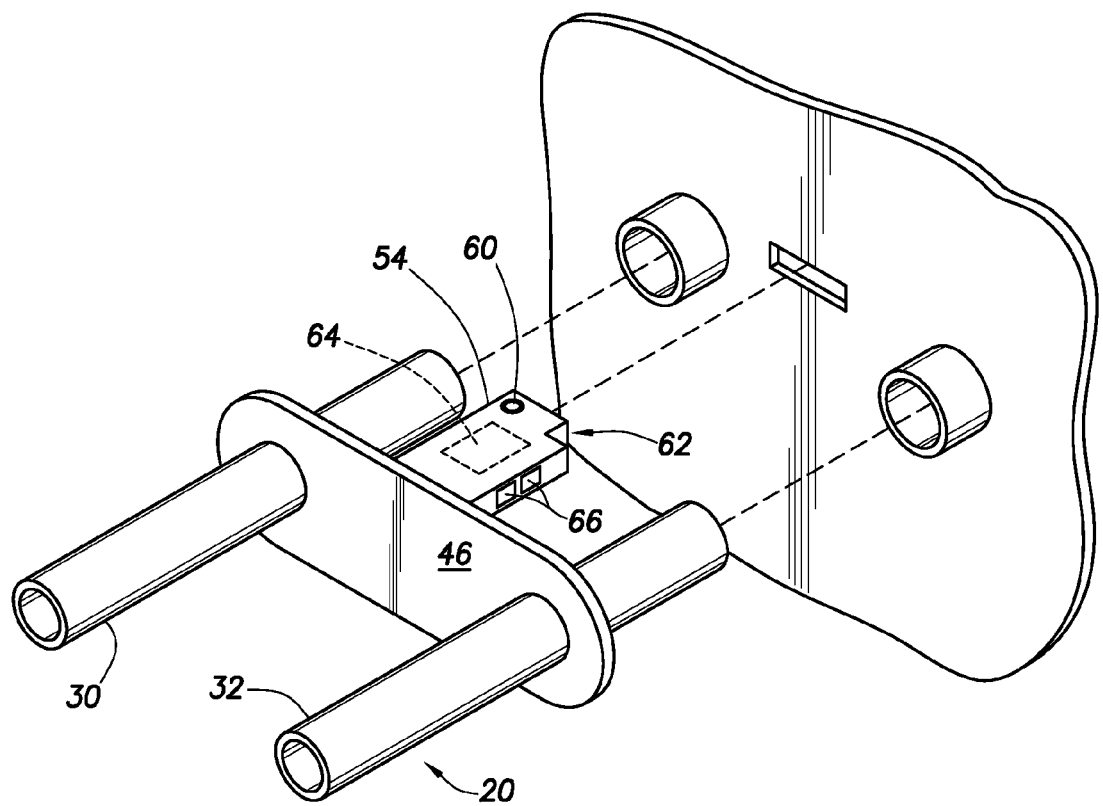
FIG. 4 illustrates hose connections that also identify the mask, in accordance with some embodiments.

FIG. 4 illustrates embodiments where the bifurcated nasal cannula 20 identifies its manufacturer and/or type. In particular, the tab 54 of the bracket 46 has features that identify the bifurcated nasal cannula to which the hoses 30 and 32 couple. The term "features" in this specification and in the claims is used broadly to encompass not only physical features (e.g., aperture 60 or notch 62), but the term features also comprises any mechanism that identifies the nasal mask (e.g., embedded electronic device 64). The embedded electronic device 64 in some embodiments is a serial read only memory (ROM) which electronically couples to and communicates with a processor of the bilateral positive airway pressure device by way of electrical contacts 66. In alternative embodiments, the embedded electrical device 64 is a radio frequency identification (RFID) tag which is read by the bilateral positive airway pressure device. In yet further alternative embodiments, the tab 54 has identifying indicia on its outer surface, such as a color coding scheme or bar code, that is read by the processor of the test device 10. Notice also that in addition to supporting the features which identify the nasal cannula, the tab 54 can also serve the purpose of ensuring that the cannula couples to the test device in only one orientation, as discussed above.

Figure 5:
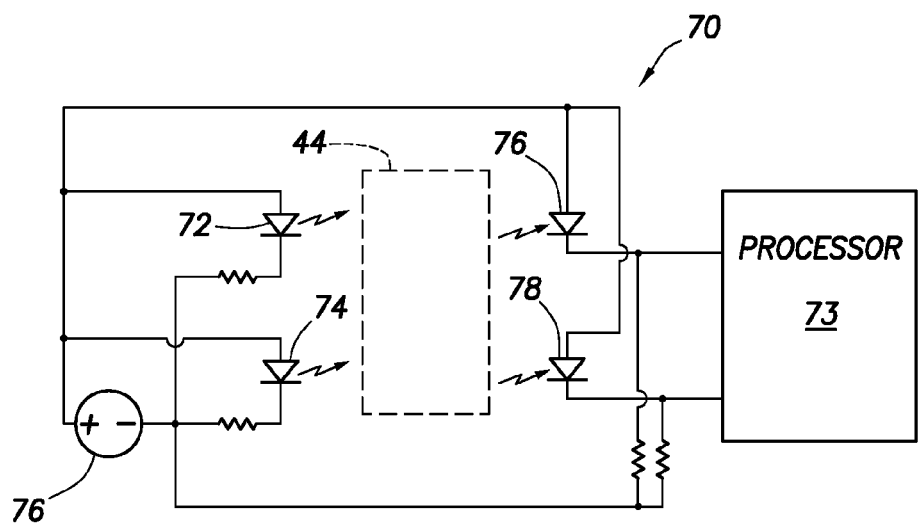
FIG. 5 illustrates an electrical circuit in accordance with some embodiments.

FIG. 5 illustrates a circuit 70 which couples to an illustrative processor 73. The processor 73 performs, in whole or in part, the diagnosis or pre-diagnosis performed by the test device 10. The circuit 70 illustrated in FIG. 5 may be part of the test device 10, and is enabled for use with features of the tab 54 being aperture 60 and/or notch 62. In particular, the circuit 70 comprises light emitting diodes 72 and 74. Electrical current supplied from source 76 flows through the diodes creating light (not necessarily visible). The light from the light emitting diode 72 and 74 is configured to shine across the aperture, the aperture illustrated by dashed line 44. The circuit 70 further comprises photo diodes 76 and 78. Photo diodes 76 and 78 are arranged to be in operational relationship with the light emitting diode 72 and 74 respectively. While the illustrative circuit of FIG. 5 shows only two light detection paths, any number of light emitting diodes and photo diodes implementing any number of light detection paths may be equivalently used. As the tab 54 is inserted through the key aperture 44, the light path between the corresponding light emitting diode and photo diode is selectively broken, and the type of nasal cannula to which the hose system 20 is attached may be identified by the pattern of broken and unbroken lights paths. For example, if the light path between the light emitting diode 72 and photo diode 76 is broken, the photo diode 76 ceases conducting, and therefore the processor 73 sees a low voltage or logic zero input. Likewise, if the tab 54 has an aperture 60 or notch 62 such that the light path is unbroken in spite of the presence of the tab 54, the photo diode conducts and the processor 73 sees a high voltage or a logic one. In the illustrative case of FIG. 5 having two light paths, three different nasal cannulas may be identified (assuming that two unbroken light paths indicate that no cannula has been connected to the test device).

Figure 6:
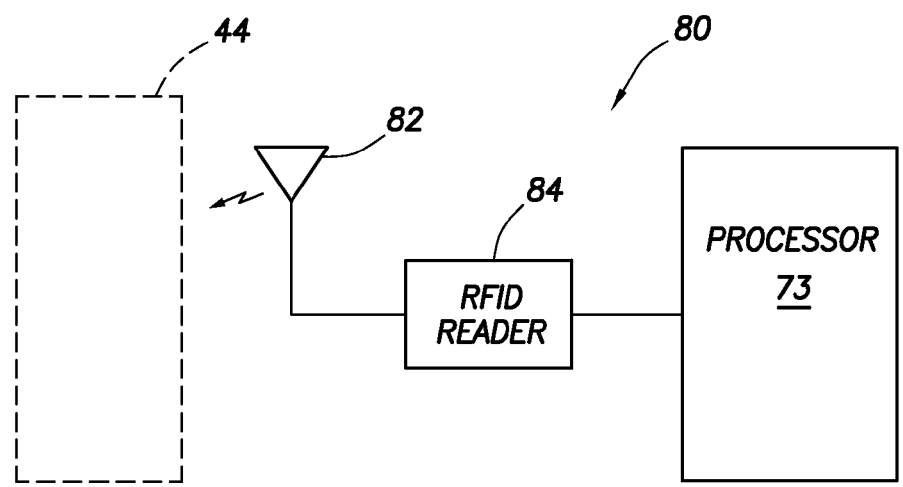
FIG. 6 illustrates an electrical circuit in accordance with some embodiments.

FIG. 6 illustrates alternative embodiments where the feature used to identify the nasal cannula is an RFID tag. In particular, the system 80 comprises a tag antenna 82 coupled to a RFID reader 84. The RFID reader 84 and tag antenna 82 work together to interrogate an RFID tag coupled on the device end of a nasal cannula. In some embodiments, the RFID tag may reside on the tab 54, and thus the antenna 82 may be in operational relationship to the aperture 44. In other embodiments, the RFID tag may reside at any location proximate to the device-end of the cannula. Once the data payload of the RFID tag is read by the RFID reader, the RFID reader passes the information along to the processor 73 which may then compensate readings based on the physical characteristics of the cannula.

Figure 7:
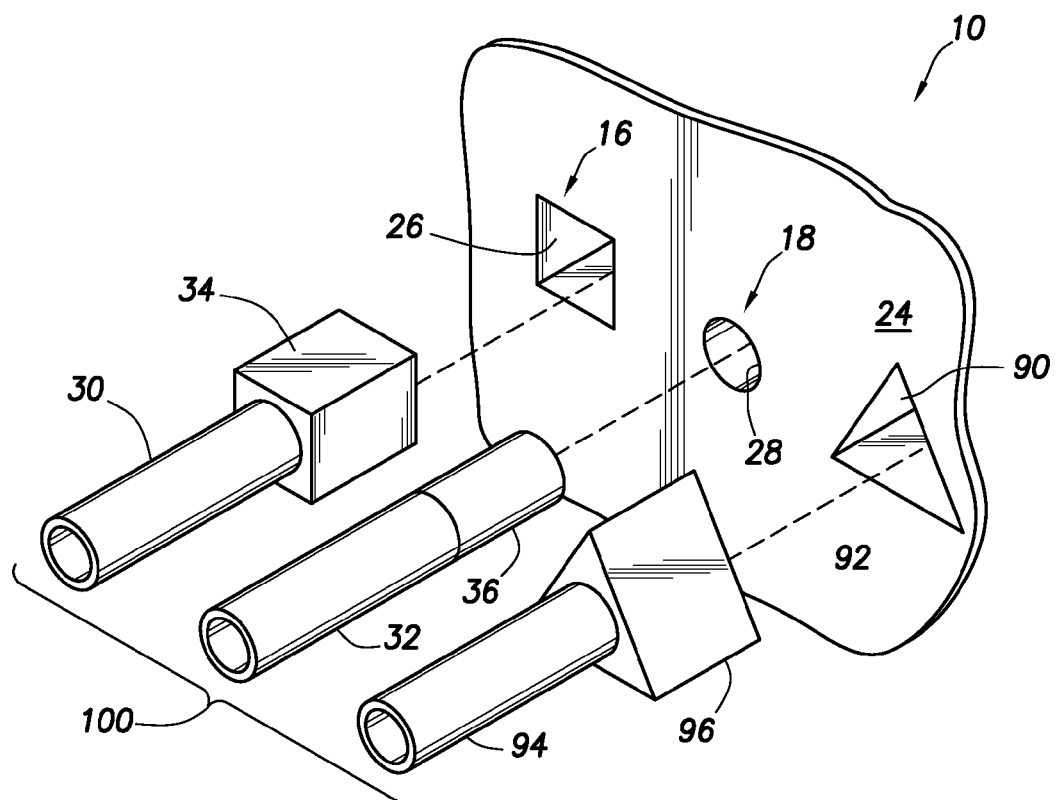
FIG. 7 illustrates hose connections in accordance with some embodiments.

The various embodiments discussed to this point are based on use of a bifurcated (two-tube) cannula. In alternative embodiments, the test device 10 may also monitor airflow through a patient's mouth, and thus a three-tube cannula may be used. U.S. Pat. No. 7,007,694 titled "Nasal Cannula," assigned to the same assignee as this specification and incorporated by reference herein as if reproduced in full below, is illustrative of a nasal cannula that may be used to monitor respiratory airflow through a patient's nares and mouth. It may as important to properly couple the tube associated with the mouth to a proper port on the test device 10. FIG. 7 illustrates system where device-end fittings of a three-tube cannula ensure proper orientation. In particular, FIG. 7 illustrates a partial view of an exterior 24 of a test device 10. The illustrative exterior in these embodiments has three outlet ports 16, 18 and 90, which in these embodiments comprise apertures 26, 28 and 92. The apertures 26, 28 and 92 fluidly couple to devices internal to the test device 10, such as pressure sensors and/or flow sensors. FIG. 7 also illustrates a portion of the bifurcated nasal cannula 100 comprising a first hose 30, a second hose 32 and a third hose 94. Each of the hoses 30, 32 and 94 has a device-end fitting 34, 36 and 96, respectively. As illustrated in FIG. 7, the device-end fitting 34 is configured to fluidly couple to the aperture 26, but because of the difference in aperture shape the device-end fitting 34 will not couple to the apertures 28 or 92. Likewise, the device-end fitting 36 is configured to fluidly couple to the aperture 28, but because of the difference aperture shape the device-end fitting 36 will not fluidly couple the aperture 26 or 92. Finally, the device-end fitting 96 is configured to fluidly couple to the aperture 92, but because of the difference in aperture shape the device-end fitting 96 will not fluidly couple to apertures 26 and 28. In this way, the three-tube cannula 100 cannot be fluidly coupled to the test device 10 in an incorrect order. While FIG. 7 shows an illustrative aperture shapes, other shapes and configurations may be equivalently used.

Figure 8:
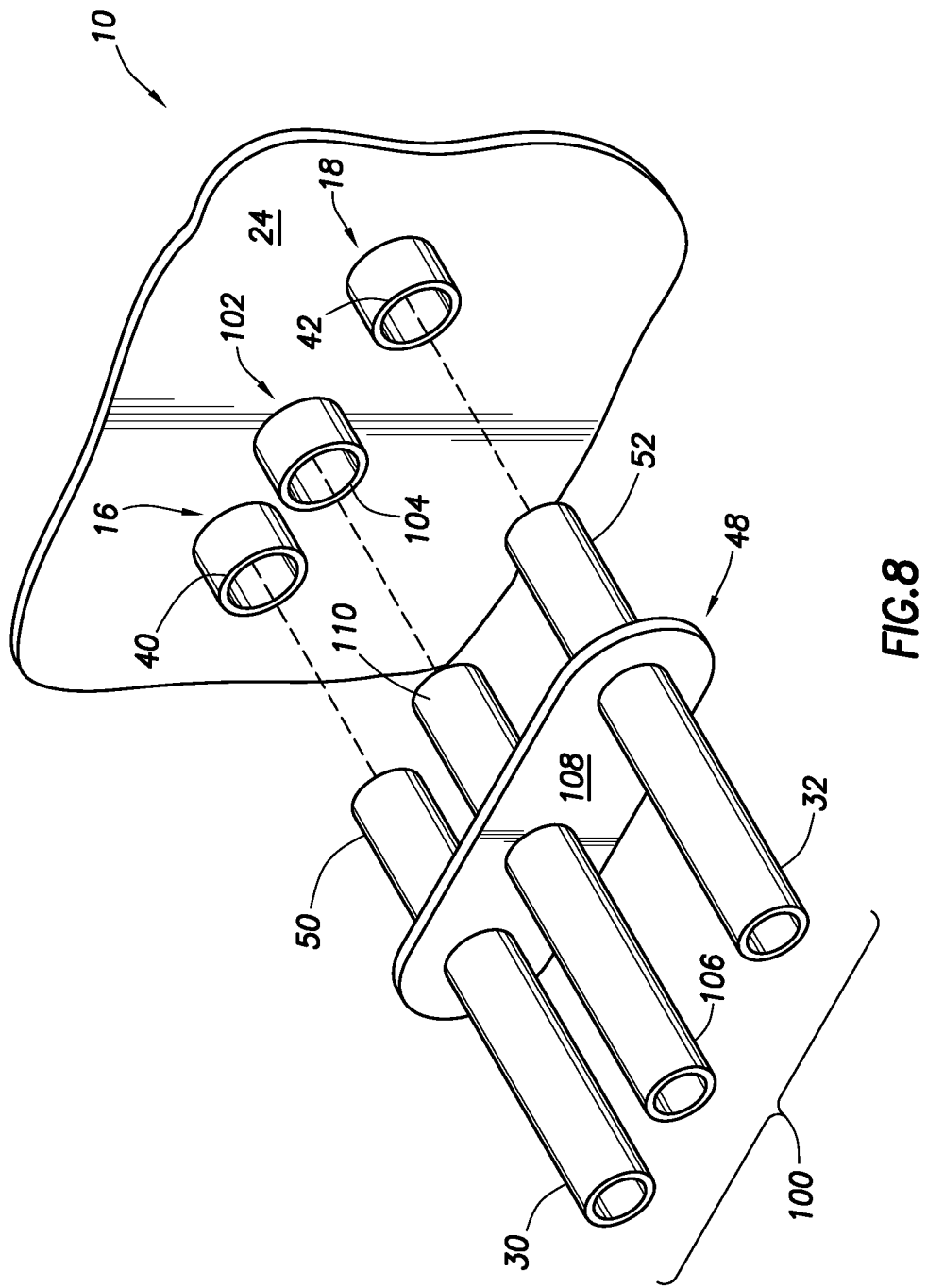
FIG. 8 illustrates hose connections in accordance with some embodiments.

FIG. 8 illustrates alternative embodiments that ensure proper coupling of the three-tube cannula 100 to the test device 10. In particular, FIG. 8 illustrates a partial view of the exterior 24 of the test device 10. The illustrative exterior has three outlet ports 16, 18 and 102, which in these embodiments comprises male connections 40, 42 and 104, respectively. Female connections may be equivalently used. The connections 40, 42 and 104 couple one each devices to internal to the test device 10, such as pressure sensors and/or flow sensors. FIG. 8 also illustrates a portion of the three-tube nasal cannula 100 comprising a first hose 30, second hose 32 and third hose 106. A bracket 108 mechanically (though not fluidly) couples the hoses 30, 32 and 106 together on the device-end 48. Each of the hoses 30, 32 and 106 has a device-end fitting 50, 52 and 110, respectively; however, the device-end fittings may be similar in these embodiments because the bracket 108 and placement of the hoses on the bracket 108 work together with the test device 10 to ensure that the house is coupled in only one orientation. In particular, the middle hose is offset from the center such that cannula 100 couples to the test device 10 in only one orientation. Although illustrative FIG. 8 shows the hoses to be co-planar, in alternative embodiments the hoses may reside at different elevations, and indeed the different elevations may ensure that the hoses couples to the test device in only one orientation. Moreover, although a tab on the bracket and corresponding aperture in the test device are not strictly needed in the embodiments of FIG. 8, a tab may nonetheless be used as the mechanism to identify the cannula, as discussed above.

The above discussion is meant to be illustrative of the principles and various embodiments of the present invention. Numerous variations and modifications will become apparent to those skilled in the art once the above disclosure is fully appreciated. For example, ensuring the hoses connect in only one orientation may involve each connection comprising a male-type connector having a different diameter. Thus, while one hose may physically fit over a connector designed for a smaller diameter hose, the larger diameter hose will not seal, thus informing the user inappropriateness of the connection. It is intended that the following claims be interpreted to embrace all such variations and modifications.

What is claimed is:

1. A system comprising:
   a test device comprising:
      a first port;
      a second port; and
      a key aperture disposed through the test device;
   a nasal cannula comprising:
      a first hose configured to fluidly couple on a device-end to the first port, and the first hose configured to fluidly couple between the first port and a first naris of a patient;
      a second hose configured to fluidly couple on a device-end to the second port, and the second hose configured to fluidly couple between the second port and a second naris of the patient;
      a bracket configured to hold the device-ends of the first and second hoses in a fixed relationship; and
      a tab on the bracket;
      wherein the nasal cannula is configured such that the first hose can only couple to the first port and the second hose can only couple to the second port;
      wherein the key aperture and the tab of the bracket are configured such that the tab extends into the aperture when the hoses are fluidly coupled to the ports; and
      wherein the test device is configured to read features of the tab that identify the nasal cannula; and
      wherein the key aperture and the tab of the bracket enable fluid coupling of the hoses to the ports in only one orientation.

2. The system as defined in claim 1 wherein the test device further comprises:
   a source of light proximate to the aperture; and
   a light detector proximate to the aperture and in operational relationship to the source of light;
   wherein the test device is configured to read a feature of the tab based on whether the tab allows light from the source of light to reach the light detector.

3. The system as defined in claim 1 wherein the test device further comprises:
   an antenna in operational relationship to the aperture; and a radio frequency identification (RFID) reader circuit coupled to the antenna;

wherein the test device is configured to read a RFID tag coupled to the tab.

4. The system as defined in claim 1 wherein the test device further comprises:

an antenna; and a radio frequency identification (RFID) reader circuit coupled to the antenna;

wherein the test device is configured to read a RFID tag coupled on the device-end of the nasal cannula.

5. The system as defined in claim 1 wherein the tab on the bracket identifies at least one selected from the group consisting of: manufacturer of the nasal cannula; type of nasal cannula; internal diameter of a tube of the nasal cannula; and length of the nasal cannula.

6. A nasal cannula comprising:

a first hose configured to fluidly couple on a device-end to a first port of a test device and on a patient-end to a first naris of a patient;

and a second hose configured to fluidly couple on a device-end to a second port of the test device and on a patient-end to a second naris of the patient, wherein the second hose is fluidly independent from the first hose;

a bracket configured to hold the device ends of the first and second hoses in a fixed relationship; and a tab on the bracket, and the tab having a feature that identifies the nasal cannula;

wherein the nasal cannula is configured such that the first hose will only couple to the first port and the second hose will only couple to the second port; and wherein the tab is configured to enable coupling of the hoses to the ports in only one orientation.

7. The nasal cannula as defined in claim 6 wherein the feature further comprises one or more selected from the group consisting of: an aperture; a notch; a read only memory device; a radio frequency identification tag; a bar code; and a color.

8. The nasal cannula as defined in claim 6 wherein the tab on the bracket identifies at least one selected from the group consisting of: manufacturer of the nasal cannula; type of nasal cannula; internal diameter of a tube of the nasal cannula; and length of the nasal cannula.

* * * * *